US006887222B2

(12) United States Patent
Mandzij et al.

(10) Patent No.: US 6,887,222 B2
(45) Date of Patent: May 3, 2005

(54) OSTOMY POUCH WITH BIAS MEMBERS AND CLOSURE MEANS

(75) Inventors: Taras Mandzij, Gurnee, IL (US); Michael A. Metz, Chicago, IL (US); Timothy A. Friske, Round Lake Beach, IL (US); Michael S. Cherry, Glenview, IL (US)

(73) Assignee: Hollistser Incorporated, Libertyville, IL (US)

( * ) Notice: Subject to any disclaimer, the term of this patent is extended or adjusted under 35 U.S.C. 154(b) by 0 days.

(21) Appl. No.: 10/283,801

(22) Filed: Oct. 30, 2002

(65) Prior Publication Data

US 2003/0153882 A1 Aug. 14, 2003

Related U.S. Application Data

(60) Provisional application No. 60/355,489, filed on Feb. 8, 2002.

(51) Int. Cl.$^7$ .................................................. A61F 5/44
(52) U.S. Cl. ..................................... 604/332; 604/277
(58) Field of Search ........................ 604/277, 332–345, 604/355; 383/46–48

(56) References Cited

U.S. PATENT DOCUMENTS

| | | | | |
|---|---|---|---|---|
| 3,408,705 A | * | 11/1968 | Kayser et al. | ................. 24/452 |
| 3,523,534 A | | 8/1970 | Nolan | |
| 3,690,320 A | * | 9/1972 | Riely | .......................... 604/333 |
| 3,825,005 A | | 7/1974 | Fenton | |
| 4,233,977 A | * | 11/1980 | Mattson | ...................... 604/335 |
| 4,441,659 A | | 4/1984 | Marklund | |
| 4,869,725 A | * | 9/1989 | Schneider et al. | .......... 604/408 |
| 5,457,855 A | | 10/1995 | Kenney et al. | |
| 5,968,024 A | * | 10/1999 | Freeman | ..................... 604/334 |
| 6,336,918 B1 | | 1/2002 | Olsen et al. | |
| 6,544,241 B2 | * | 4/2003 | Morton | ....................... 604/334 |
| 6,589,221 B1 | * | 7/2003 | Olsen et al. | ................. 604/332 |
| 6,726,667 B2 | * | 4/2004 | Leise et al. | .................. 604/339 |
| 2003/0028160 A1 | * | 2/2003 | Leise et al. | .................. 604/334 |

FOREIGN PATENT DOCUMENTS

| | | |
|---|---|---|
| GB | 2 000 683 | 1/1979 |
| GB | 2 346 328 | 8/2000 |

OTHER PUBLICATIONS

International Search Report; PCT/US 02/34773 dated Feb. 26, 2003.

* cited by examiner

*Primary Examiner*—Larry I. Schwartz
*Assistant Examiner*—Michael G. Bogart
(74) *Attorney, Agent, or Firm*—Marshall, Gerstein & Borun LLP

(57) ABSTRACT

A drainable ostomy pouch having sidewalls of flexible sheet material defining a cavity therebetween and a downwardly-extending neck portion terminating in a discharge opening that is closed by folding the neck portion upwardly and opened by unfolding the neck portion downwardly. Each of the sidewalls of the neck portion is provided with a transversely-extending bias member that is formed of stiff but flexible, springlike plastic material. The bias members are normally flat so as to be in straight parallel closed condition but are openable under inwardly-directed finger pressure applied to their opposite ends to cause them to bow outwardly away from each other. The pouch also includes a two-part fastening system for holding the neck portion in upwardly-folded condition, the system including a first fastener part located along the outer surface of one of the sidewalls of the neck portion and a second fastener part located along the outer surface of the other sidewall of the neck portion, the fastener parts having outwardly-projecting interengageable locking elements that are brought into interlocking engagement when the neck portion is fully folded.

17 Claims, 8 Drawing Sheets

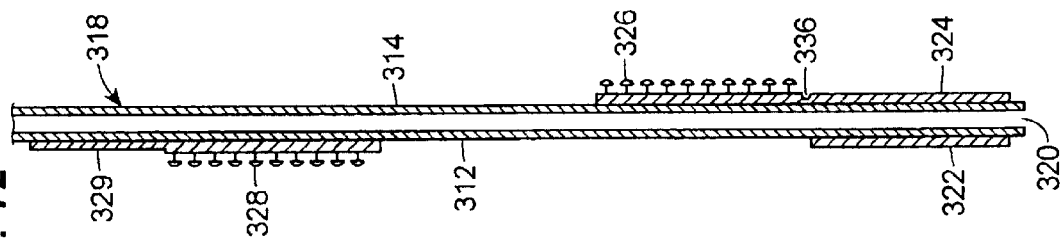
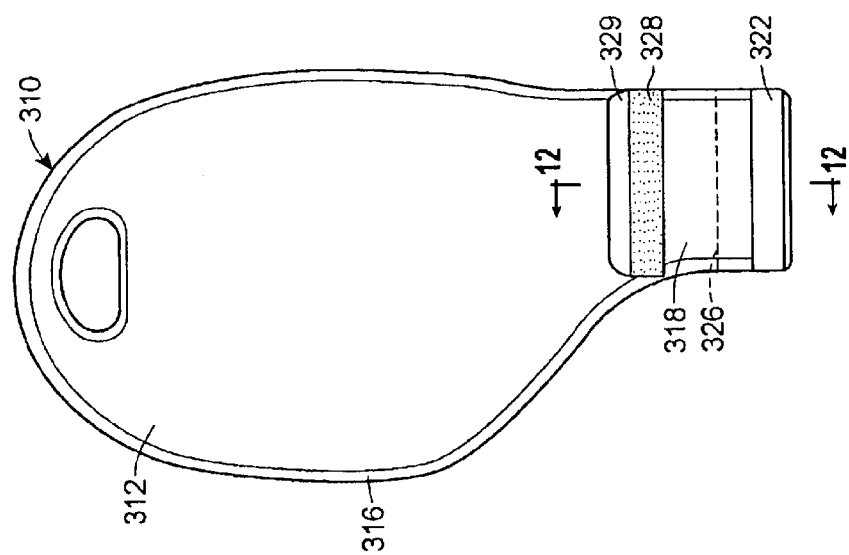
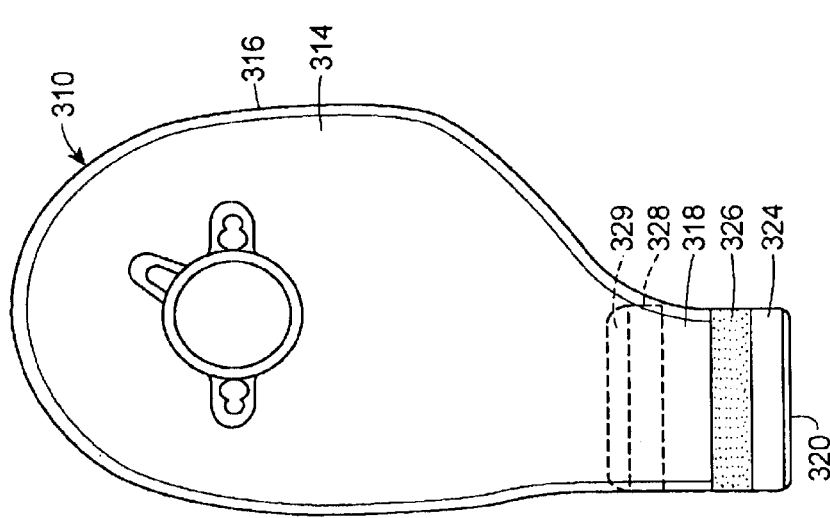

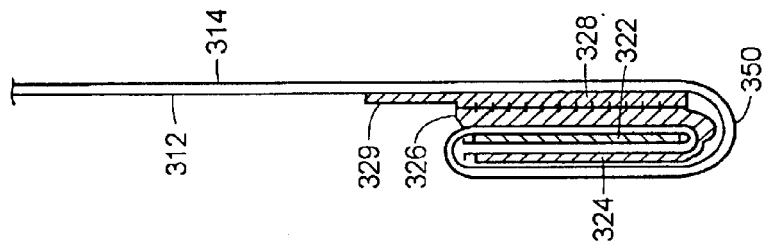
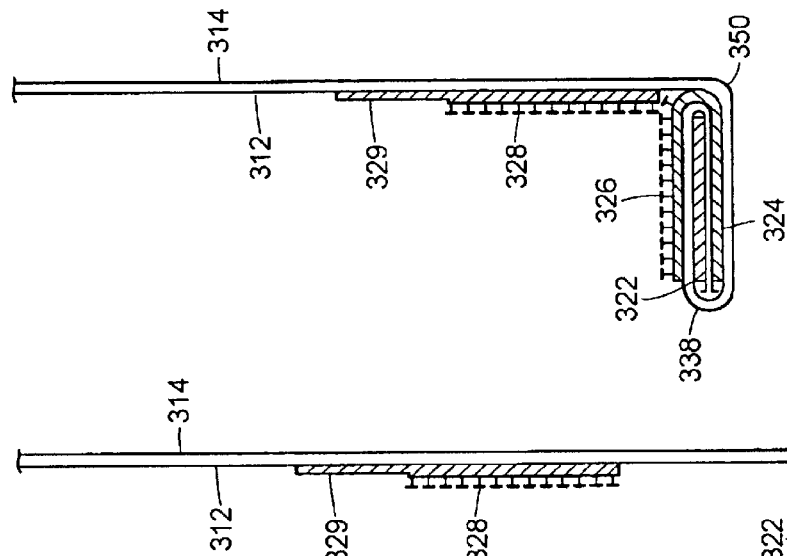
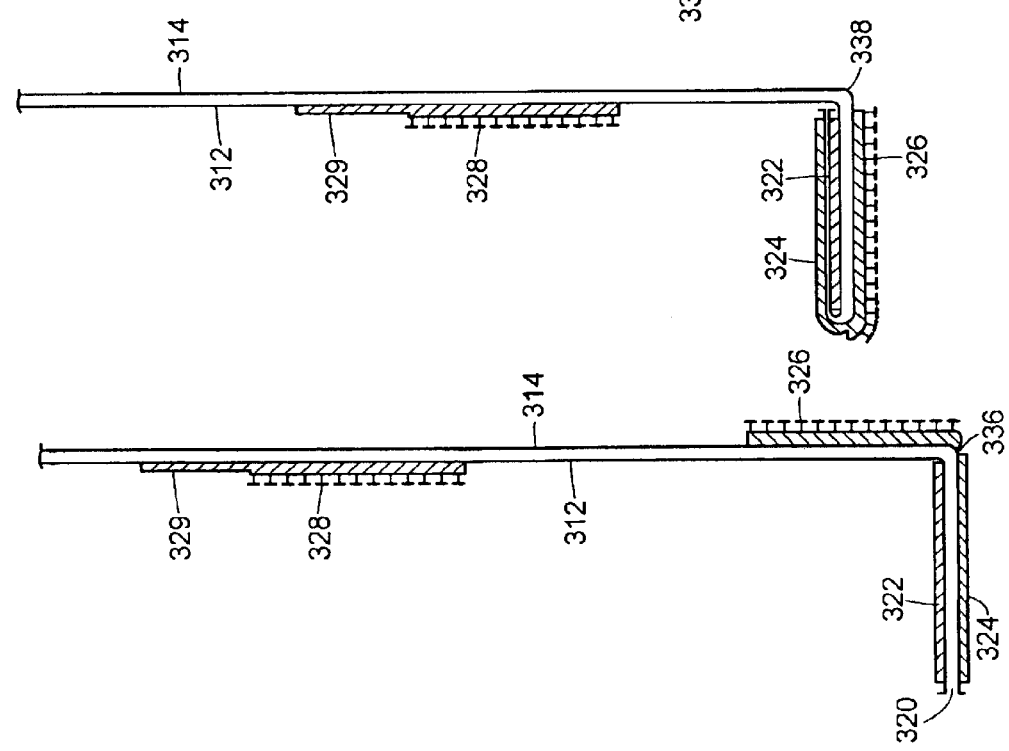

OSTOMY POUCH WITH BIAS MEMBERS AND CLOSURE MEANS

RELATED APPLICATION

This application claims priority from U.S. Provisional Patent application Ser. No. 60/355,489 filed Feb. 8, 2002.

BACKGROUND

Drainable ostomy pouches are well known as shown, for example, in Nolan U.S. Pat. No. 3,523,534 and Jensen et al. U.S. Pat. No. 4,441,659. Such a pouch typically has flat opposing sidewalls secured together along their edges and defining a chamber for receiving body waste material. One of the walls is provided with a stoma-receiving opening, and means are provided for securing the pouch to a patient's abdomen so that waste discharge from the stoma is received in the cavity. At its lower end, the drainable pouch has a discharge opening for draining waste material, usually provided at the end of a narrowed neck portion. Closure means is provided for maintaining the discharge opening in sealed condition until such time as waste material is to be drained from the pouch. The closure means may take the form of a clamp, as in the aforementioned Nolan patent, or some device for securing the neck portion in upwardly-rolled condition. As will be appreciated, conventional wire ties or wraps have also been used for that purpose.

A drainable pouch is reusable following periodic emptying of waste material, but cleaning is necessary prior to reuse so that effective sealing can be assured and odors emanating from the resealed pouch can be avoided. Users often encounter difficulty and discomfort in unsealing, emptying, cleaning and resealing drainable pouches because of the direct exposure to waste material and because the manipulations may require greater dexterity than a patient, particularly an elderly patient, can provide. Adding to the problem is the fact that residual amounts of solid and/or liquid waste matter at the lower end of a drainage pouch tends to block or hold the walls of the pouch together, making cleaning of the inside surfaces adjacent the drain opening even more difficult.

SUMMARY OF THE INVENTION

The drainable ostomy pouch of the invention has conventional sidewalls of flexible sheet material joined along their edges to define a downwardly extending neck portion terminating in a discharge opening. The discharge opening is closed by folding the neck portion upwardly and opened by folding the neck portion downwardly for draining the contents from the cavity. Each of the sidewalls of the neck portion is provided with a transversely-extending bias member in the form of a closure strip of flexible but stiff or springlike polymeric material. The strips located along opposite sidewalls adjacent to or near the discharge opening are normally flat and disposed in straight parallel closed relation but are openable under inwardly directed finger pressure applied to opposite ends thereof. By applying inwardly directed finger pressure, the bias members or closure strips are caused to be bowed away from each other to hold the discharge opening in an open condition for draining the contents from the cavity.

In one form of the drainable ostomy pouch, the bias members are laterally offset from one another whereas in another form of the pouch, the bias members substantially conform in size and shape and they extend continuously or uninterruptedly from one joined edge to the other. In yet another form of the drainable ostomy pouch, the bias members substantially conform in size and shape but extend less than the entire distance from one joined edge to the other, such members being centered relative to the discharge opening.

In another respect, the drainable ostomy pouch has a discharge opening that is placed in closed condition by folding the pouch in a first direction (away from the wearer's body) and is placed in an open condition by unfolding the pouch in a second, opposite direction. A two-part fastener is provided for selectively holding the discharge opening in the closed condition, and it includes a first part associated with the pouch generally adjacent to or near the discharge opening and a second part associated with the pouch spaced further from the discharge opening than the first part. More specifically, the second fastener part is spaced from the discharge opening to require folding the pouch until the first fastener part comes into confronting relation with the second fastener part for engagement therewith.

In yet another respect, the drainable ostomy pouch has a two-part fastener associated with a neck portion leading to the pouch's discharge opening. The fastener comprises a first fastener strip with locking means along its outer surface disposed in a first position relative to the discharge opening and a second fastener strip with interengagable locking means disposed in a second position relative to the discharge opening. Most advantageously, the fastener strips each may have an array of identical mushroom-shaped locking elements along its outer surface, and the neck portion is foldable at least twice for causing the elements of the first and second fastener strips, located along opposite sides of the neck, to be brought into interlocking engagement to hold the neck portion in folded condition.

Other advantages and features of the invention will become apparent from the following specification when considered in view of the accompanying drawings.

DRAWINGS

FIG. 10 is a front elevational view of another form of drainable ostomy pouch in accordance with the present invention.

FIG. 11 is a rear elevational view of the drainable ostomy pouch of FIG. 10 in fully unfolded condition.

FIG. 12 is an enlarged and somewhat schematic cross-sectional view of the drainable ostomy pouch taken along the line 12—12 in FIG. 11.

FIG. 13 is a cross-sectional view similar to FIG. 12 but showing the neck portion at the beginning of a folding operation. For clarity of illustration, the walls of the neck portion are shown slightly spaced apart and each is represented only by a single line.

FIG. 14 is a cross-sectional view of the neck portion of the pouch of FIG. 10 after a first fold has been made and at the start of a second fold.

FIG. 15 is a cross-sectional view of the neck portion of the pouch of FIG. 10 after a second fold has been made and at the beginning of a third fold.

FIG. 16 is a cross-sectional view of the neck portion of the pouch of FIG. 10 in fully folded condition.

DETAILED DESCRIPTION OF PREFERRED EMBODIMENTS

Figure 1:
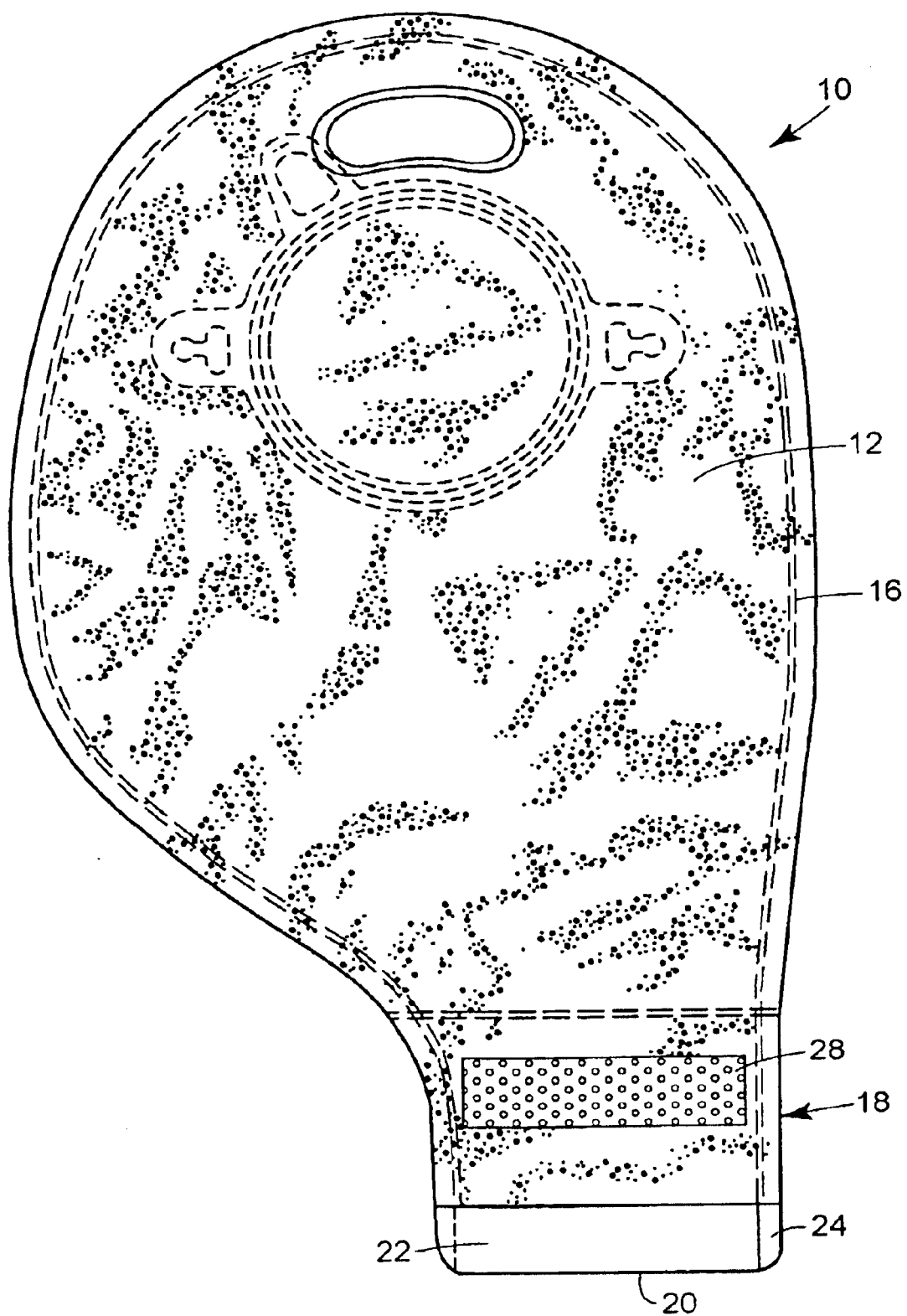
FIG. 1 is a front elevational view of a drainable ostomy pouch having bias members in the form of laterally offset flexible closure strips.
Figure 2:
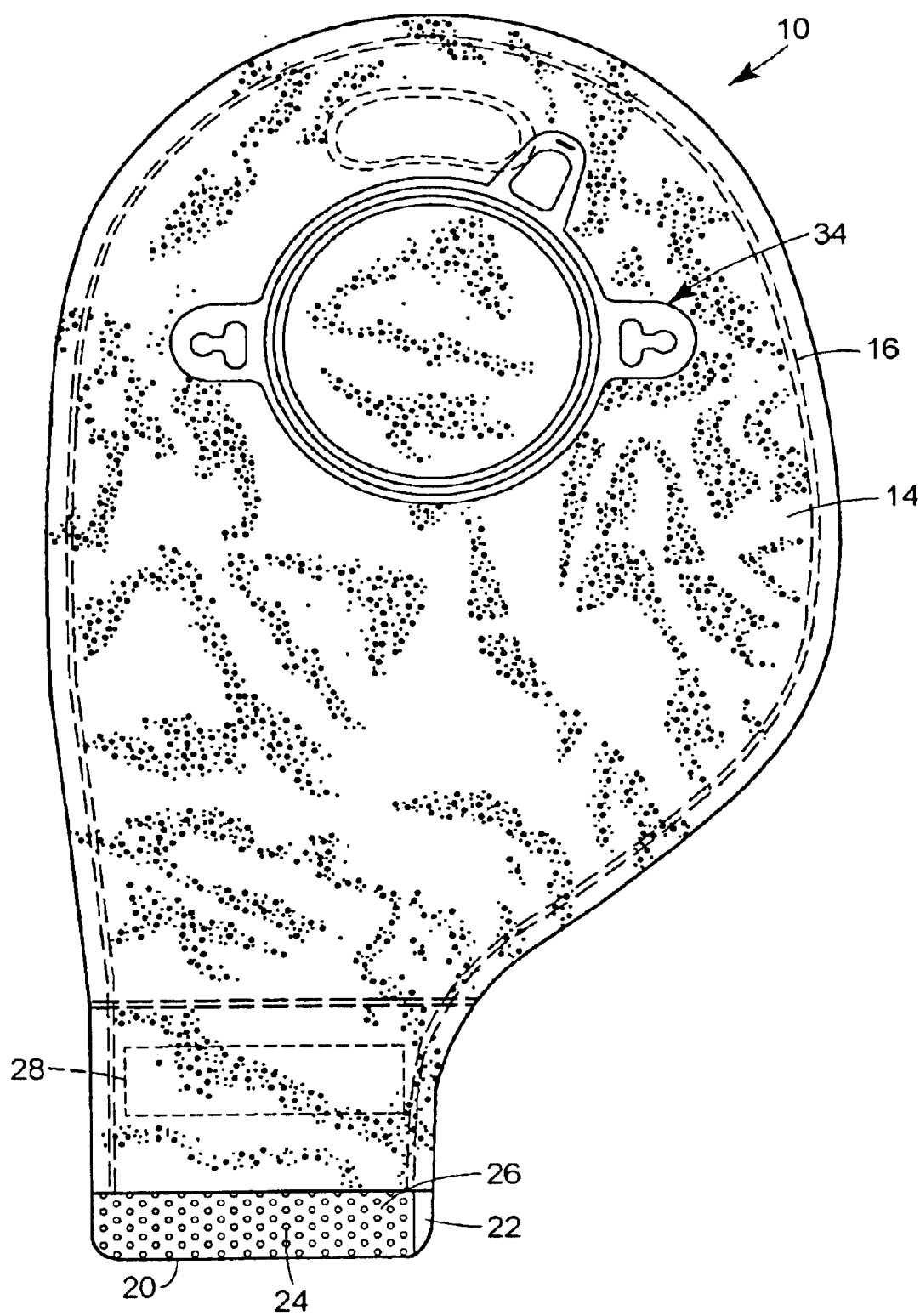
FIG. 2 is a rear elevational view of the drainable ostomy pouch of FIG. 1.

Referring to FIGS. 1 and 2 of the drawings, the numeral 10 designates a drainable ostomy pouch having generally parallel sidewalls 12 and 14. The sidewalls 12 and 14 are joined along their edges as at 16 to define a cavity therebetween. They also define a downwardly-extending neck portion 18 which terminates in a discharge opening as at 20. The neck portion 18 is shown as non-symmetrical in the drawings although it will be understood that it can be symmetrical relative to the remainder of the pouch as this forms no part of the invention. As shown in the drawings, each of the sidewalls 12 and 14 of the neck portion 18 is provided along its outer surface with a transversely-extending and generally rectangular bias member in the form of closure strips 22 and 24. The strips are located at or adjacent to the discharge opening 20 so as to be in generally overlapping back-to-back parallel relation.

Figure 3A:
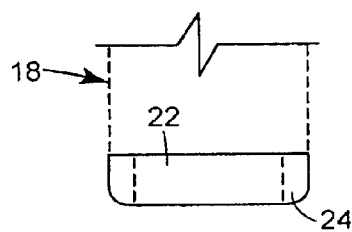
FIG. 3A is a schematic front elevational view of the neck portion of a pouch having laterally offset closure strips.
Figure 3B:
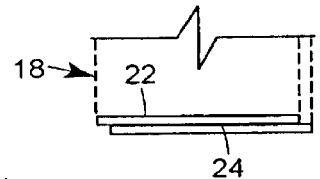
FIG. 3B is an end elevational view of the laterally offset strips of FIG. 3A in closed condition.
Figure 3C:
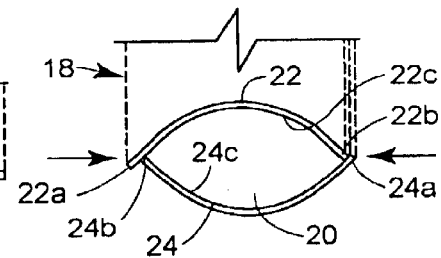
FIG. 3C is an end elevational view of the laterally offset strips of FIG. 3A in open condition.

As will be appreciated by referring to FIGS. 3A–3C, the bias members 22 and 24 are stiff but flexible, springlike plastic (i.e., polymeric) strips that normally are flat and disposed in straight parallel relation to maintain opening 20 in substantially closed condition. However, they can be flexed to an open condition by applying inwardly directed finger pressure to opposite ends of strips 22 and 24 to cause them to be bowed away from each other with smoothly arched curvatures as shown in FIG. 3C. In this manner, the discharge opening can be opened and held in open condition for draining the contents from the cavity of pouch 10.

Figure 6A:
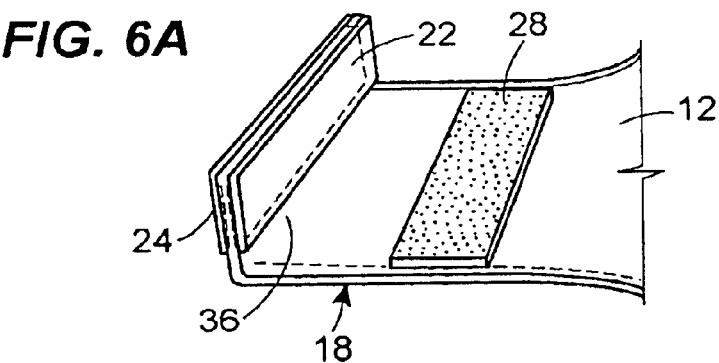
FIGS. 6A–6D are schematic views illustrating the steps of securing a discharge opening of a drainable ostomy pouch in folded condition.
Figure 6B:
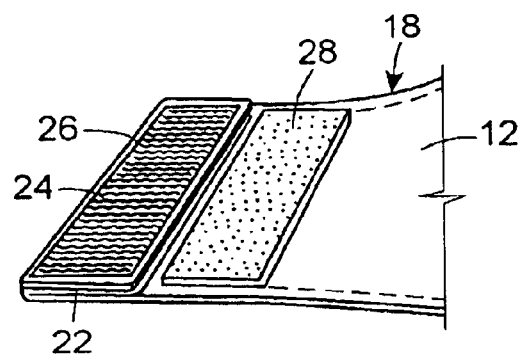
Figure 6C:
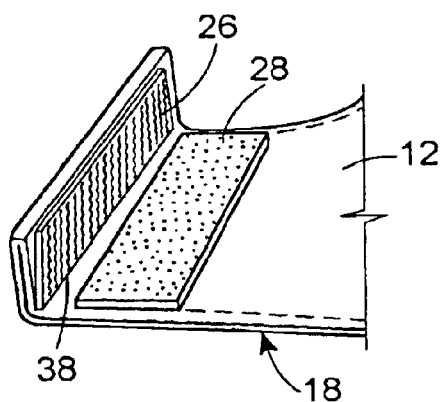
Figure 6D:
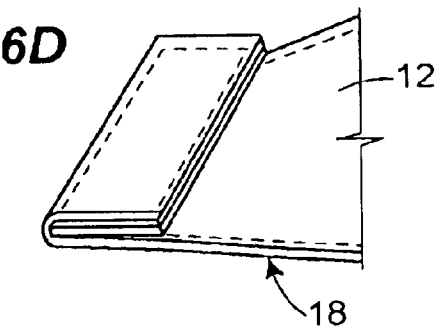

Referring once again to FIGS. 1 and 2, the drainable ostomy pouch will also be seen to include a two-part fastener system for selectively holding the neck portion 18 in upwardly folded condition as best shown in FIG. 6D. The two-part fastener system includes a first part 26 associated with one of the closure strips 24 on one side of the neck portion and a second part 28 at a location spaced from the discharge opening along the opposite side of the neck portion. The second fastener part 28 is spaced from the discharge opening at a distance sufficient to require folding the neck portion 18 upwardly at least twice (see FIGS. 6A–6C). In this manner, the first fastener part 26 is brought into confronting relation with the second fastener part 28 for engagement therewith, selectively holding the neck portion 18 in its upwardly folded condition.

In the illustrated embodiment, the first fastener part 26 is associated with an outwardly facing surface of the closure strip 24 whereas the second fastener part 28 is associated with an outwardly facing surface of the opposite wall of the neck portion 18 and substantially conforms in size and shape with closure strip 24. More specifically, the first and second fastener parts 26 and 28 are advantageously complementary materials, one being carried by closure strip 24 across one wall of the neck portion and the other by the outer surface of the other wall of the neck portion which, when interlocked together, have a retention force for maintaining the neck in folded condition absent a disengagement force sufficient to overcome the retention force.

With the arrangement illustrated in FIGS. 1 and 2, the sidewalls 12 and 14 are formed of a flexible plastic film that is substantially water and gas impermeable. One of the sidewalls 14 (the proximal or bodyside wall) is provided with a stoma-receiving opening 32 surrounded by means for attaching the drainable ostomy pouch 10 to a patient. The attaching means may take the form of a coupling device generally designated 34 provided for detachably securing the drainable pouch 10 to an adhesive faceplate which together define a two-piece appliance. Alternatively, the pouch may be a one-piece appliance with an integral and non-separable faceplate.

Figure 4A:
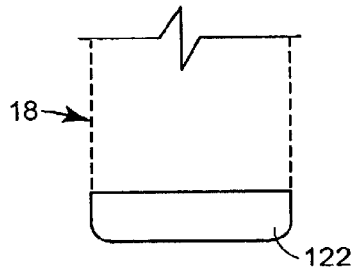
FIG. 4A is a schematic front elevational view of the neck portion of a pouch having full-width closure strips.
Figure 5A:
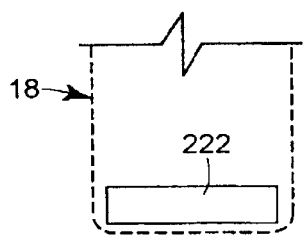
FIG. 5A is a schematic front elevational view of the neck portion of pouch having centered strips of a length less than the full width of the neck portion of the pouch.

Referring now to FIGS. 3A, 4A, and 5A, it will be seen that the bias members or closure strips 24, 26 may take several different forms such as the three that have been illustrated and will be described below.

FIGS. 3A and 3B illustrate bias members in the form of asymmetrical closure strips 22 and 24 which are normally flat and laterally offset from one another so as to be in straight parallel closed condition, i.e., they are adjacent one another separated only by the sidewalls 12 and 14 to which they are secured, with one end of each strip projecting laterally (in relation to neck portion 18) beyond the corresponding end of the other strip. However, the closure strips 22 and 24 can be opened under inwardly-directed finger pressure applied to opposite ends of the strips to cause them to be bowed away from each other to hold the discharge opening 20 in open condition. As shown in FIG. 3C, inwardly directed finger pressure against the ends 22a and 24a causes the opposite ends 22b and 24b to bear against the corresponding flat surfaces 24c and 22c of the other of the closure strips 24 and 22, respectively.

Figure 4B:
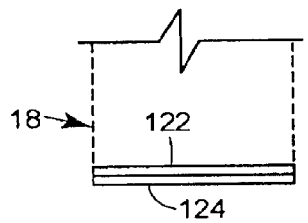
FIG. 4B is an end elevational view of the strips of FIG. 4A in closed condition.
Figure 4C:
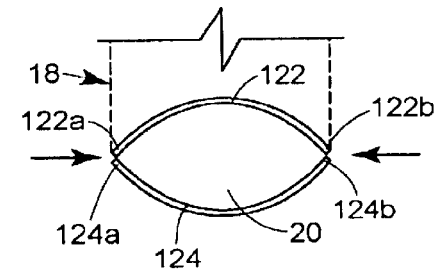
FIG. 4C is an end elevational view of the strips of FIG. 4A in open condition.
Figure 5B:
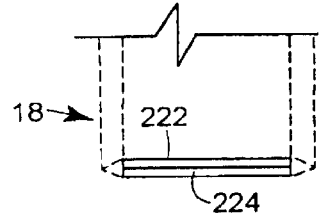
FIG. 5B is an end elevational view of the centered strips of FIG. 5A in closed condition.
Figure 5C:
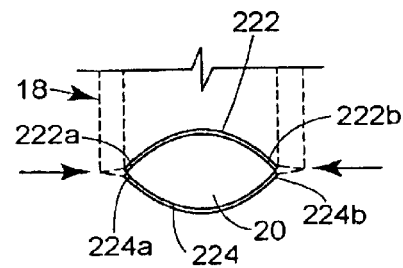
FIG. 5C is an end elevational view of the centered strips of FIG. 5A in open condition.

FIGS. 4A and 4B illustrate bias members or closure strips 122 and 124 which are normally flat, substantially conform with each other in size and shape, and extend continuously or uninterruptedly from edge to edge so as to be in straight parallel closed condition, i.e., adjacent one another but separated only by the sidewalls 12 and 14 to which they are secured. However, the closure strips 122 and 124 can be opened under inwardly-directed finger pressure applied to opposite ends of the strips to cause them to be bowed away from each other (FIG. 4C) and to hold the discharge opening in an open condition. As shown in FIG. 4C, inwardly directed finger pressure against the ends 122a, 124a and 122b, 124b of the strips causes the corresponding ends 122a, 124a and 122b, 124b to bear against one another to bow the closure strips 122 and 124 outwardly for holding the drainage opening 20 in open condition. Unlike the bias members 22 and 24 illustrated in FIGS. 3A and 3B which are offset from one another, the bias members 122 and 124 may need slight manipulation, or the presence of at least a small amount of waste material in the neck portion, to cause them to start being bowed away from each other as endwise squeezing force is applied. FIGS. 5A–5B illustrate bias members in the form of closure strips 222 and 224 which are normally flat, substantially conform in size and shape, and are centered, but extend less than the entire distance between the edges of the neck portion 18 so as to be in straight parallel closed positions, i.e., adjacent each other but separated only by the sidewalls 12 and 14 to which they are secured. As in the embodiment of FIGS. 4A–4C, the bias members or closure strips 222 and 224 can be opened under inwardly directed finger pressure applied to opposite ends of the strips to cause them to be bowed away from each other to hold the discharge opening 20 in open position. As shown in FIG. 5C, and in essentially the same manner as in FIG. 4C, inwardly-directed finger pressure against the ends 222a, 224a and 222b, 224b of the bias members 222 and 224 causes the corresponding ends 222a, 224a and 222b, 224b to bear against one another to bow the bias members outwardly for holding the drainage opening 20 in open position. Unlike the bias members 22 and 24 illustrated in FIGS. 3A and 3B which are offset from one another, the closure strips 222 and 224 which are centered relative to the edges may need slight manipulation or the presence of at least a small amount of waste material in the neck portion to cause them to start being bowed away from each other so as to open the discharge opening 20 as squeezing force is applied.

As will be appreciated, FIGS. 3A–3C, 4A–4C, and 5A–5C illustrate three distinct, but effective, sets of bias members or closure strips for placing and holding the discharge opening of a drainable ostomy pouch 10 in open condition for draining the contents from the cavity thereof.

The closure strips 22,24; 122, 124; and 222, 224 are formed of any stiff but flexible polymeric material that is springlike and shape-recoverable to serve as bias members that return to straight, parallel and closed conditions in the absence of inwardly-directed finger pressure such as, for example, a polyolefin such as polypropylene. Since the springiness and shape-recoverability of the strips causes them to straighten when inwardly-directed finger pressure is reduced, a user, by varying such finger pressure, may easily and selectively control the rate of discharge of waste material through the discharge opening. Each strip is non-porous and non-absorbent, may be secured to the sidewalls 12 and 14 (preferably to the outer surfaces of those sidewalls) or may be imbedded in such sidewalls. Because such strips are stiff, and non-absorbent, they are readily manipulated in use and are generally incapable of absorbing liquid and solid waste material.

Figure 19:
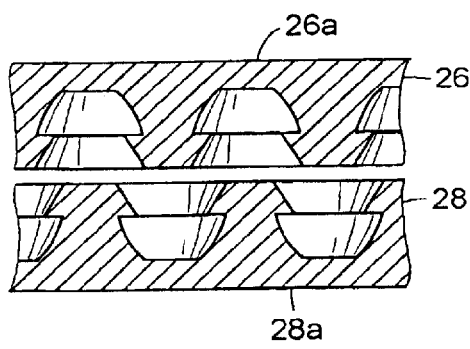
FIG. 19 is an enlarged detail view of the engagement elements provided by the first and second fastener parts on opposite sidewalls of the pouch, the engagement elements being shown in disengaged condition.
Figure 20:
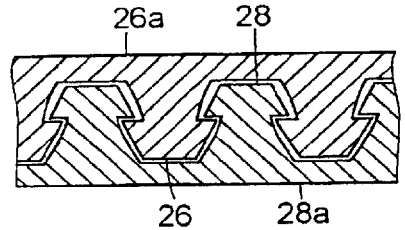
FIG. 20 is an enlarged view similar to FIG. 19 but showing the engagement elements in interlocking relation.

In a preferred embodiment, the first and second fastener parts 26 and 28 comprises a polypropylene fastener of the type sold under the trademark DUOTEC by G. Binder GmbH & Co. Holzgerlingen, Germany which is stated in product literature to work on the principle of interlocking mushroom elements. By using strips of this synthetic material for the first and second fastener parts 26 and 28, the discharge opening can be maintained in closed position (FIG. 6D) absent a disengagement force sufficient to overcome the retention force which produces an auditory and tactile disengagement indication. FIGS. 19 and 20 illustrate that the interlocking first and second fastener parts 26 and 28 include spaced mushroom-shaped projections that are formed integrally with base layers 26a and 28a, respectively. Since the two interlocking components are identical, physically-distinguishable male/female components are not required. Also, because no absorbent or fabric-like material is utilized, the opposing surfaces, with their arrays of identical mushroom-shaped projections, do not absorb waste material and may be easily cleaned after a pouch-draining operation. Among the attributes for this material is its ability to provide a solid connection when pressed firmly together, its characteristic locking action that provides a user with a tactile (also audible) signal when the parts are interlocked, and its ability to be repeatedly reopened in lengthwise or crosswise directions. Accordingly, the utilization of fastener parts with identical arrays of mushroom-shaped interlocking elements constitutes an important feature of a drainable ostomy pouch embodying this invention, although it is to be understood that other types of fastening means may be used which lack at least some of the attributes and advantages described above such as, for example, hook and loop fasteners as marketed under the Velcro trademark, various snaps or interlocking fasteners, or pressure-sensitive adhesive coatings that permit repeated separation and reconnection.

Also, while the material utilized in the fastener sold under the DUOTEC trademark is polypropylene, it will be understood that other polymeric materials having similar properties may be employed.

Referring to FIGS. 6A–6D, the second fastener part 28 is preferably spaced from the discharge opening 20 by a distance sufficient to require folding the neck portion 18 upwardly at least twice to bring the first fastener part 26 into confronting interlocking relation with the second fastener part 28 for selectively holding the neck portion 18 in its upwardly folded condition. FIG. 6A illustrates folding the neck portion 18 about a fold line as at 36 extending along the upper or proximal transverse edges of closure strips 22 and 24. FIG. 6B illustrates the neck portion after completing the fold about fold line 36. FIG. 6C illustrates a second folding of the neck portion 18 about a second transverse fold line 38 after the first fold has been completed. FIG. 6D illustrates the neck portion 18 after the second fold has been completed to bring the first fastener part 26 into interlocking relation with second fastener part 28 for selectively holding the neck portion 18 in its upwardly folded condition.

Figure 7:
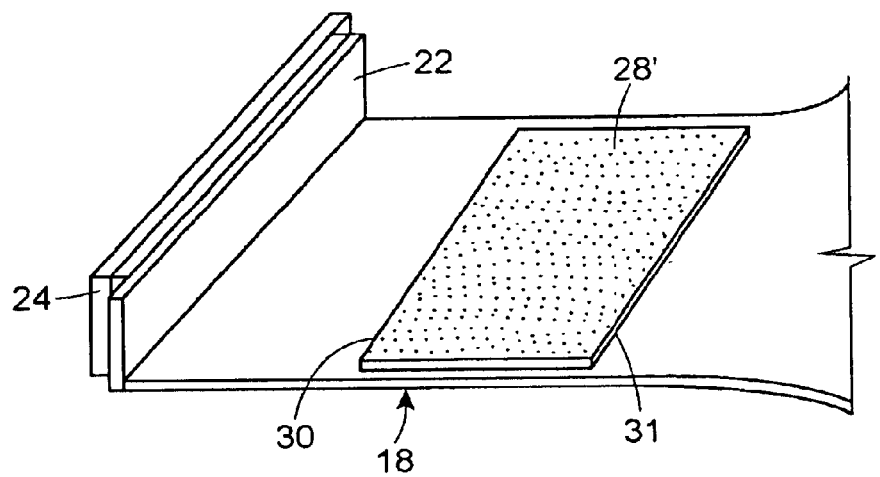
FIG. 7 is a schematic perspective view of a further form of drainable ostomy pouch at the beginning of a first folding step.
Figure 8:
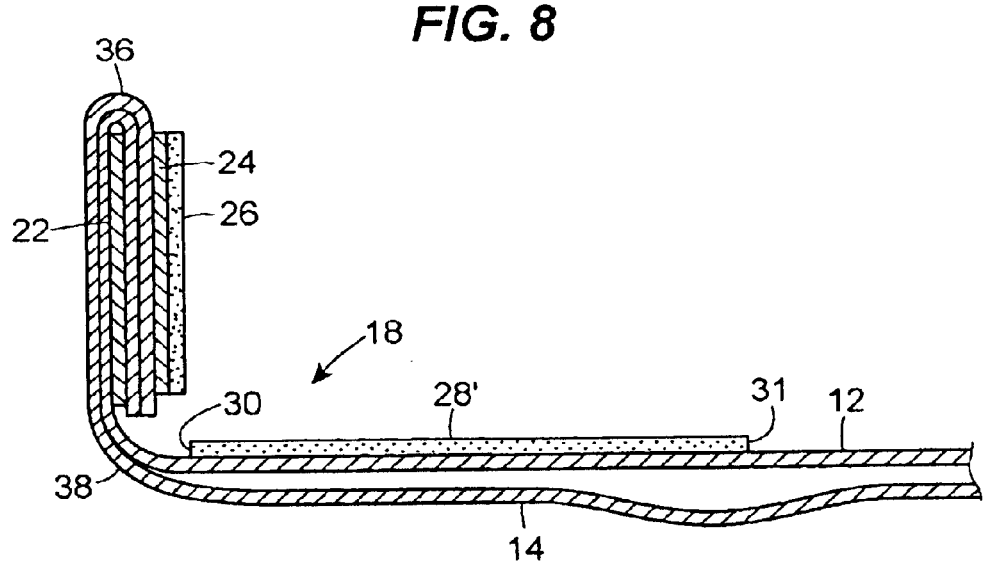
FIG. 8 is a cross-sectional view of the drainable ostomy pouch of FIG. 7 at the commencement of a second folding step.
Figure 9:
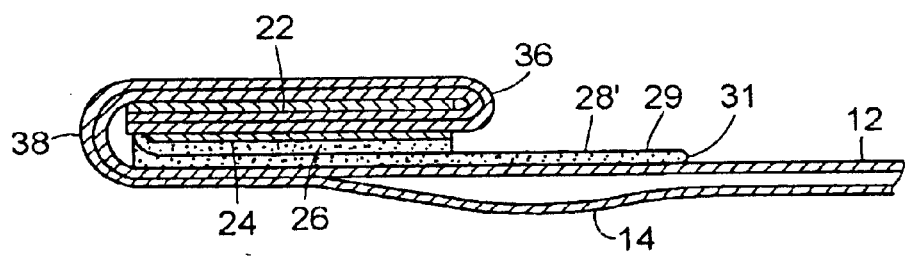
FIG. 9 is a cross-sectional view showing the drainable ostomy pouch of FIG. 7 in fully folded condition.
Figure 17:
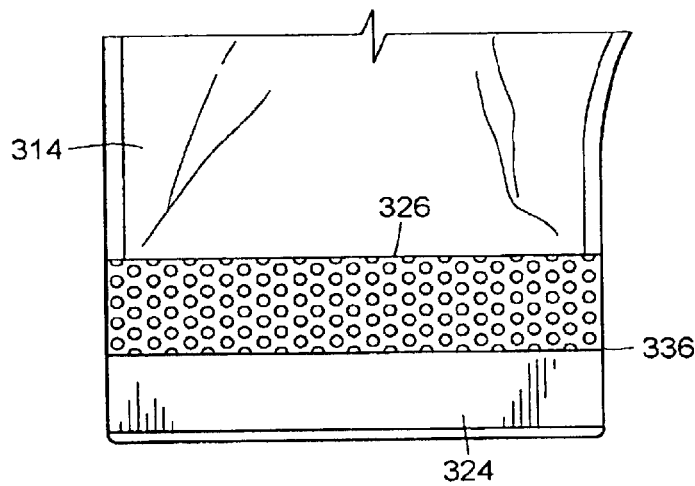
FIG. 17 is a plan view of a first fastener part associated with one of the closure strips on one sidewall of the pouch adjacent to the pouches discharge opening.

The embodiment of FIGS. 7–9 is similar to those already discussed except that second fastener part 28 has a width (a dimension extending longitudinally and proximally relative to the neck portion 18) that is substantially greater than that of the first fastener part 26. Second fastener part 28', like first fastener part 26, is preferably rectangular in shape with a distal edge 30 located as before immediately adjacent second fold line 38 (FIG. 8). When the neck portion 18 for the pouch is fully folded, as shown in FIG. 9, the second fastener part 28' therefore has a proximal surface portion 29 that remains exposed. The exposed portion 29 constitutes a proximal and integral extension of part 28' and provides visual and tactile indications that the folding of neck portion 28 has been properly completed, with the second fold 38 located immediately adjacent distal edge 30. In addition, the arrangement clearly exposes the region of the first fold 36 so that a user, by sliding his/her fingers downwardly along the surface of the exposed portion or extension 29, will encounter the second fold 36 and may easily commence an unfolding operation. Such contact may be made without risk that a user might otherwise make finger contact with proximal edge 31 and attempt to unfold the neck portion 18 by applying a lifting force directly to second fastener part 28' in an effort to peel it away from pouch wall 12. Another important benefit of utilizing a tough polymeric material for fastener part 28' is that the proximal extension 29, which is securely attached to wall 12 of the neck portion, acts to distribute forces on the wall of the pouch when the neck portion has been folded and is in use, thereby reducing localized forces that might, under extreme conditions, result in tearing of the pouch wall 12.

Since extension 29 does not engage fastener part 26 when the pouch neck is fully folded, the surface of the extension 29 may, if desired, be smooth and free of projections or interlockable elements.

As an alternative or addition to the embodiment of FIGS. 7–9, one of the two fastener parts may have a dimension measured in a direction across the neck portion 18 of the pouch that is substantially greater than the corresponding dimension of the other of the fastener parts. With this arrangement, a user may easily commence an unfolding operation by gripping the ends of the strip of greater dimension and applying a force for peeling the strip away from the other fastener part.

Referring to FIGS. 10–12 of the drawings, the numeral 310 designates another embodiment of drainable ostomy pouch having generally parallel sidewalls 312 and 314. The sidewalls 312 and 314 are joined along their edges as at 316 to define a cavity therebetween. They also define a downwardly-extending neck portion 318 which terminates in a discharge opening as at 320. Each of the sidewalls 312 and 314 in the region of the neck portion 318 is provided with a transversely-extending bias member or closure strip such as those designated as 322 and 324 in the drawings. The closure strips are located at or adjacent to discharge opening 320 so as to be in generally parallel back-to-back relation.

Like strips 22 and 24, closure strips 322 and 324 may be formed of nylon, polypropylene or any other suitable polymeric material that renders the strips stiff but flexible, non-absorbent, and generally springlike in character. It is to be understood that closure strips 322 and 324 may be configured and function in the same manner as the-described in connection with the embodiments of FIGS. 3A–3C, 4A–4C, and 5A–5C. The size, shape, and composition of strips 322 and 324 may be identical to strips 22 and 24. They extend transversely across the neck portion 318 at its discharge end and are secured to the outer surfaces of the neck portion, and are normally straight and flat (or planar) but bow outwardly away from each other, and retain such outwardly bowed condition, as long as endwise squeezing force is applied and maintained.

Immediately above closure strip 324, and similarly secured to the outer surface of sidewall 314, is the first fastener part 326 of a two-part fastener system. First part 326 takes the form of a fastener strip having outwardly-projecting locking elements which are preferably the mushroom-shaped elements described in connection with previous embodiments. In the illustration given, strips 326 and 234 are joined by an integral transversely-extending hinge 336. Perforations may be provided along the hinge line to facilitate folding of the neck portion, with the hinge 336 constituting the first fold line. It is to be understood, however, that while fastener strip 326 and closure strip 324 are shown to be connected to each other, they may instead be separate unconnected elements with the hinge line being formed solely by the line of material of sidewall 314 extending between the strips.

The second fastener part 328 of the two-part fastener system takes the form of a transverse strip with outwardly projecting interlocking elements secured to the outer surface of sidewall 312 well above the discharge opening 320 of the pouch. In the illustration given, fastener strip 328 is spaced above the discharge opening 320 a distance approximating the combined width of strips 322, 324 and 326, all three of which are of similar width. Whereas the embodiment of FIGS. 1, 2 and 6A–6D required two folding steps to bring the interlocking elements 26 and 28 into alignment and mutual engagement, the embodiment of FIGS. 10–12 requires three such folds, thereby offering even greater security for the user. Because the fastener parts or strips 326 and 328 preferably have interlocking means in the form of interfitting mushroom-shaped elements (see FIGS. 19 and 20), the user receives a tactile signal, which may even be audible, when the fastener parts are brought together and interlocked.

Figure 18:
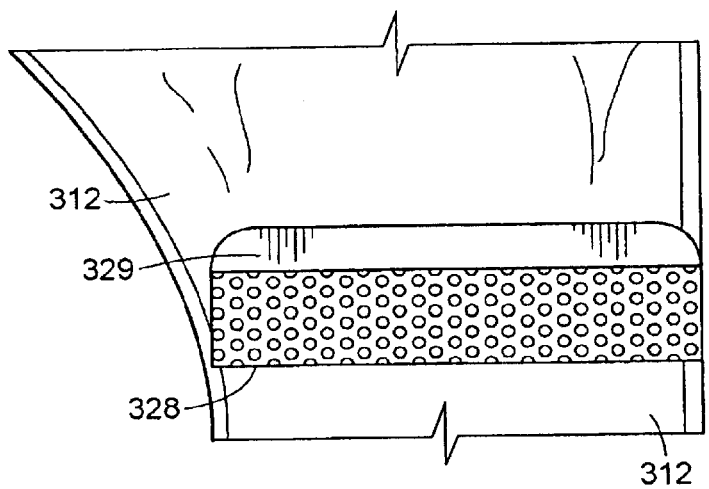
FIG. 18 is a plan view of a second fastener part spaced from the discharge opening on the opposite sidewall of the pouch of FIG. 10.

Referring to FIGS. 12 and 18, it will be noted that the second fastener part 328 includes an integral extension 329 that extends upwardly in a direction away from opening 320. In the preferred embodiment shown, extension 329 is devoid of interlocking elements and presents a relatively smooth untextured surface incapable of interlocking with the projections of the first fastener part 326. Extension 329 otherwise functions in the same manner as described in connection with extension 29 of the embodiment depicted in FIGS. 7–9.

FIGS. 13–16 illustrate the three folding steps involved in securing the neck portion 318 in folded and sealed condition. FIG. 13 depicts commencement of the first folding step with the first fold 336 occurring at the line between closure strip 324 and first fastener part or strip 326. A second fold as at 338 is formed in the next folding step illustrated in FIG. 14, and a third and final fold as at 350 occurs as shown in FIGS. 15 and 16 as the interlocking elements of first fastener part or strip 326 and second fastener part or strip 328 are brought together. Extension 329 remains exposed above the interlocked strips to provide visual and tactile indications that the folding of the neck portion has been properly completed. As a user slides his/her fingers downwardly along the surface of extension 329, the fingers will encounter the second fold as at 338 and may easily commence an unfolding operation. In addition, the extension 329 performs an important function in reinforcing sidewall 312 of the neck portion and distributing forces that would otherwise be localized along a transverse line of stress directly above the upwardly-facing second fold as at 338.

In the description of the foregoing embodiments, it has been indicated generally each of the pouches are formed of flexible plastic film such that the sidewalls are joined or sealed together along their edges in a conventional manner. However, it will be understood that each of these embodiments could be formed in another manner while enjoying the benefits of the present invention, e.g., by using a continuous tubular plastic film rather than two or more films joined together.

In all embodiments of the invention, the drainable ostomy pouches are provided with flexible shape-recoverable and non-absorbent closure or stiffening strips extending transversely across each sidewall at or adjacent to the discharge opening at the end of the neck portions. Two or more folds are required to bring the first and second fastener parts into interlocking engagement. In all embodiments, such fastener parts are located along opposite sidewalls of the neck portion and have outwardly-projecting interlocking elements, ideally in the form of mushroom-shaped projections. The closure strips at the end of the neck portion facilitate opening of the discharge openings, to hold holding such openings in open condition. The closure strips also facilitate throttling and thereby controlling the rate of flow of waste material through the openings. The closure strips further define the folds as they occur and, when folding is substantially completed, help provide bulk and stiffness to the folded neck portion to assist a user in bringing the two fastener parts into interlocking engagement. The interlocking step is therefore the final step in a sequential folding operation with the interlocking occurring at the same time that the final fold is completed.

While in the foregoing there have been set forth preferred embodiments of the invention, it will be appreciated that the details herein given may be varied by those skilled in the art without departing from the true scope and spirit of the appended claims.

What is claimed is:

1. A drainable ostomy pouch having sidewalls of flexible sheet material which define a cavity therebetween and which define a downwardly extending neck portion terminating in a discharge opening that is closed by folding the neck portion upwardly and opened by unfolding the neck portion downwardly for draining the contents from the cavity; wherein the improvement comprises a transversely-extending bias member integrally associated with each of the sidewalls adjacent the discharge opening such that the bias members are separated by the sidewalls; the bias members normally being flat so as to be in straight parallel closed condition but being moveable so as to be bowed away from each other and to have smoothly arched curvatures under inwardly directed finger pressure applied to opposite ends of the bias members to hold the discharge opening in an open position; the bias members comprising stiff but flexible, springlike shape-recoverable strips permitting selective control of the rate of discharge of the contents from the cavity by applying varying finger pressure to opposite ends thereof; and wherein the strips are generally rectangular and are offset in directions extending transversely of the neck portion so that each strip has one end portion extending beyond the corresponding end portion of the other of the offset strips.

2. The drainable ostomy pouch of claims 1, including a two-part fastening system for selectively and releasably holding the neck portion in upwardly folded condition; the system including a first fastener part located along the outer surface of one of the sidewalls of the neck portion and a second fastener part located along the outer surface of the other of the sidewalls of the neck portion; the first and second fastener parts being brought into mutual engagement and attachment when the neck portion is in its fully folded condition.

3. The drainable ostomy pouch of claim 2 in which the fastener parts have outwardly-projecting interengagable locking elements that are brought into interlocking engagement when the neck portion has been folded upwardly at least twice.

4. The drainable ostomy pouch of claims 3 in which the fastener parts comprise plastic strips that have interengageable locking elements that are mushroom-shaped.

5. The drainable ostomy pouch of claim 4 in which the fastener parts on opposite sidewalls of the neck portion have identical mushroom-shaped locking elements.

6. The drainable ostomy pouch of claim 3 in which one of the fastener parts is located closer to the discharge opening than the other of the fastener parts; the other of the fastener parts having an integral extension that is exposed and extends upwardly beyond the folded neck portion when the neck portion is fully folded.

7. The drainable ostomy pouch of claim 6 in which the integral extension is devoid of interlocking elements.

8. A drainable ostomy pouch having sidewalls of flexible sheet material which define a cavity therebetween and which define a downwardly-extending neck portion terminating in a discharge opening that is closed by folding the neck portion upwardly and opened by unfolding the neck portion downwardly for draining the contents from the cavity; wherein the improvement comprises a two-part fastener system including a first fastener strip secured to the outer surface of the neck portion on one of the sidewalls of flexible sheet material and a second fastener strip secured to the outer surface of the neck portion on the other of the sidewalls of flexible sheet material; the first fastener strip being disposed closer to the discharge opening than the second fastener strip and defining first and second transverse fold lines for folding and unfolding the neck portion to close and open the discharge opening; the first and second fastener strips having outwardly-projecting interlockable elements that are brought into selective and releasable interlocking engagement when the neck portion has been folded upwardly at least twice about the first fastener strip to bring the first and second fastener strips into engagement.

9. The drainable ostomy pouch of claim 8 in which the interlockable elements of the first and second fastener parts are identical.

10. The drainable ostomy pouch of claim 9 in which the interlockable elements of the first and second fastener parts are mushroom-shaped.

11. The drainable ostomy pouch of claim 8, 9 or 10 in which the sidewalls of the neck portion are each provided with a transversely-extending bias member located adjacent the discharge opening; the bias members normally being flat so as to be in straight parallel closed condition but being openable under inwardly-directed finger pressure applied to opposite ends of the bias members to cause the bias members to be bowed away from each other to hold the discharge opening in an open position for draining the contents from the cavity.

12. The drainable ostomy pouch of claim 11 in which the bias members comprise closure strips of stiff but flexible, non-absorbent, springlike plastic material.

13. The drainable ostomy pouch of claim 12 in which the closure strips are generally rectangular and are offset in directions extending transversely of the neck portion so that each strip has one end portion extending beyond the corresponding end portion of the other of the strips.

14. The drainable ostomy pouch of claim 12 in which the strips are generally rectangular and conform in size and shape with each strip extending uninterruptably from one side edge to the other side edge of the neck portion.

15. The drainable ostomy pouch of claim 12 in which the strips are generally rectangular and conform in size and shape, with each strip having a length measured transversely of the neck portion that is less than the width of the neck portion; the strips being centered relative to the neck portion and the discharge opening.

16. The drainable ostomy pouch of claim 8 in which one of the fastener parts is located closer to the discharge opening than the other of the fastener parts; the other of the fastener parts having an integral extension that is exposed and extends upwardly beyond the folded neck portion of the pouch when the neck portion is fully folded.

17. The drainable ostomy pouch of claim 16 in which the integral extension is devoid of interlocking elements.

* * * * *

UNITED STATES PATENT AND TRADEMARK OFFICE
CERTIFICATE OF CORRECTION

PATENT NO. : 6,887,222 B2  Page 1 of 1
DATED : May 3, 2005
INVENTOR(S) : Taras Mandzij et al.

It is certified that error appears in the above-identified patent and that said Letters Patent is hereby corrected as shown below:

Column 9,
Line 53, "claims" should read -- claim --.

Column 10,
Line 42, "claim" should read -- claims --.

Signed and Sealed this

Eleventh Day of October, 2005

JON W. DUDAS
*Director of the United States Patent and Trademark Office*